US009846137B2

(12) United States Patent
Bhansali et al.

(10) Patent No.: US 9,846,137 B2
(45) Date of Patent: Dec. 19, 2017

(54) SENSORS FOR THE DETECTION OF ANALYTES

(71) Applicants: Shekhar Bhansali, Weston, FL (US);
Pandiaraj Manickam, Miami, FL (US)

(72) Inventors: Shekhar Bhansali, Weston, FL (US);
Pandiaraj Manickam, Miami, FL (US)

(73) Assignee: THE FLORIDA INTERNATIONAL UNIVERSITY BOARD OF TRUSTESS, Miami, FL (US)

( * ) Notice: Subject to any disclaimer, the term of this patent is extended or adjusted under 35 U.S.C. 154(b) by 0 days.

(21) Appl. No.: 15/242,082

(22) Filed: Aug. 19, 2016

(65) Prior Publication Data
US 2017/0227486 A1 Aug. 10, 2017

Related U.S. Application Data

(60) Provisional application No. 62/292,919, filed on Feb. 9, 2016.

(51) Int. Cl.
G01N 27/327 (2006.01)
G01N 33/543 (2006.01)
G01N 33/74 (2006.01)

(52) U.S. Cl.
CPC ..... G01N 27/3278 (2013.01); G01N 33/5438 (2013.01); G01N 33/743 (2013.01)

(58) Field of Classification Search
CPC ............. G01N 27/327; G01N 27/3275; G01N 27/3278
See application file for complete search history.

(56) References Cited

U.S. PATENT DOCUMENTS

2013/0306485 A1* 11/2013 Varghese ........... G01N 27/3277
205/162

OTHER PUBLICATIONS

Kan et al., "Molecular imprinting polymer electrosensor based on gold nanoparticles for theophylline recognition and determination," Microchim Acta (2010) 171:423-429.*
Yuan et al., "Electrochemical sensor based on molecularly imprinted membranes at platinum nanoparticles-modified electrode for determination of 17β-estradiol," Biosensors and Bioelectronics 29 (2011) 29-33.*
Yadav et al., "A review on determination of steroids in biological samples exploiting nanobio-electroanalytical methods," Analytica Chimica Acta 762 (2013) 14-24.*

(Continued)

Primary Examiner — Alexander Noguerola
(74) Attorney, Agent, or Firm — Saliwanchik, Lloyd & Eisenschenk

(57) ABSTRACT

The subject invention provides materials and methods of fabricating and using an electrochemical biosensor for continuous detection of biological analytes. In a specific embodiment, the biosensor detects a given analyte when the analyte binds with a molecularly imprinted polymer (MIP) matrix immobilized atop a sensing substrate eliminating the need for a redox probing agent commonly found in electrochemical biosensors. Furthermore, the detection sensitivity of the biosensor is enhanced by modifying the electrode surface with a plurality of nanoscopic metallic structures. Advantageously, technologies provided herein can be used in a variety of low-power electronics for wearable applications.

8 Claims, 9 Drawing Sheets

(56) References Cited

OTHER PUBLICATIONS

Miss Phatsaraporn Angkornram, Graduate Seminar II, summary of presentation entitled "Molecularly Imprinted Polymer-Hybrid Electrochemical Sensor for the Detection of β-estradiol", date: Tuesday, Sep. 2, 2014.*

Xie et al., "Surface Molecular Self-Assembly for Organophosphate Pesticide Imprinting in Electropolymerized Poly(p-aminothiophenol) Membranes on a Gold Nanoparticle Modified Glassy Carbon Electrode," Anal. Chem. 2010, 82, 241-249.*

Huang et al., "Fabrication of gold/polypyrrole core/shell nanowires on a flexible substrate for molecular imprinted electrochemical sensors," RSC Adv. 2014, 4, 62393-62398.*

Kan et al., "Imprinted electrochemical sensor of dopamine recognition and determination based on a carbon nanotube/polypyrrole film", Electrochemica Acta 63 (2012) 69-75.*

Freund et al., "Anion-Excluding Polypyrrole Films," Talanta vol. 38, No. 1, pp. 95-99 1991.*

Witkowski et al., "Effect of Electrode Substrate on the Morphology and Selectivity of Overoxidized Polypyrrole Films," Anal. Chem. 1991, 63, 622-626.*

Özkorucuklu et al., "Voltammetirc Behaviour of Sulfamethoxazole on Electropolymerized-Molecular Imprinted Overoxidzed Polypyrrole," Sensors 2008, 8, 8463-8478.*

Dopamine entry on Open Chemistry Database of the U.S. National Library of Medicine—National Center for Biotechnology Information downloaded from https://pubchem.ncbi.nlm.nih.gov/compound/dopamine on May, 23, 2017.*

First four pages of "dopamine" entry in the Open Chemistry Database at the National Center for Biotechnology Information Downloaded from https://pubchem.ncbi.nlm.nih.gov/compound/dopamine#section=Top on Aug. 2, 2017.*

Basu, M., et al., "Nano-biosensor development for bacterial detection during human kidney infection: Use of glycoconjugate-specific antibody-bound gold NanoWire arrays (GNWA)." *Glycoconjugate Journal*, 2004, 21: 487-496.

Chianella, I., et al., "Direct replacement of antibodies with molecularly imprinted polymer (MIP) nanoparticles in ELISA—development of a novel assay for vancomycin." *Anal Chem.*, Sep. 2013, 85(17): 8462-8468.

Connolly, S., et al., "Effects of Ligand-Receptor Geometry and Stoichiometry on Protein-Induced Aggregation of Biotin-Modified Colloidal Gold." *J. Phys. Chem. B*, 2001, 105(11): 2222-2226—Abstract only.

Fullam, S., et al., "Carbon Nanotube Templated Self-Assembly and Thermal Processing of Gold Nanowires." *Advanced Materials*, Oct. 2000, 12(19): 1430-1432—Abstract only.

Karimian, N., et al., "An ultrasensitive molecularly-imprinted human cardiac troponin sensor." *Biosensors and Bioelectronics*, Jul. 2013, 50: 492-498.

Li, B.L., et al., "A novel strategy for selective determination of D-penicillamine based on molecularly imprinted polypyrrole electrode via the electrochemical oxidation with ferrocyanide." *Sensors and Actuators B*, Jun. 2013, 186: 96-102.

Liu, Z., et al., "Single Nanoporous Gold Nanowire Sensors." *J. Phys. Chem. B*, Jan. 2006, 110: 4318-4322.

Kaushik, A. et al., "A label-free electrochemical immunosensor for beta-amyloid detection." *Analytical Methods*, 2016, 8: 6115-6120, DOI: 10.1039/c6ay01910b.

Kaushik, A. et al., "Electrochemical sensing method for point-of-care cortisol detection in human immunodeficiency virus-infected patients." *International Journal of Nanomedicine*, 2015, 10: 1-9.

Pasha, S. K., et al., "Electrochemical Immunosensing of Saliva Cortisol." *Journal of the Electrochemical Society*, 2014, 161(2): B3077-B3082, DOI: 10.1149/2.017402jes.

* cited by examiner

WE – Working electrode
RE – Reference electrode
CE – Counter electrode
100 – Three electrode design involving any shape and any metal

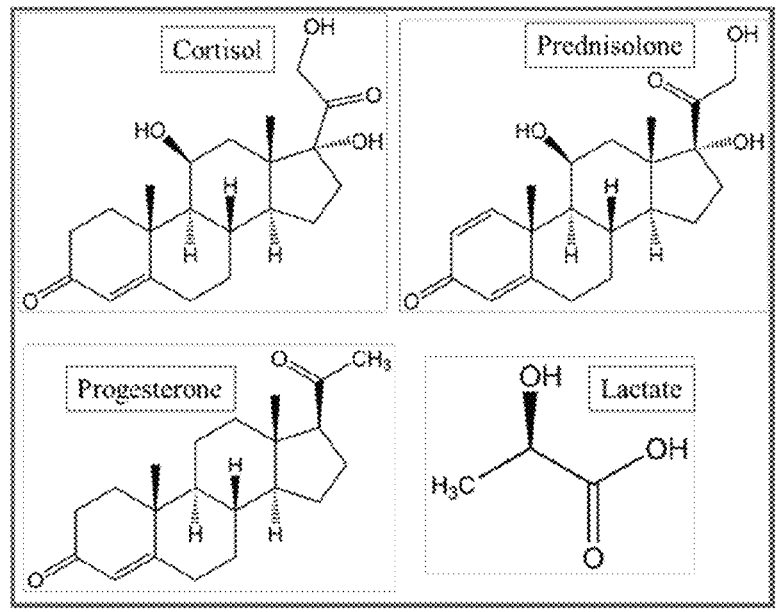
FIG. 8C
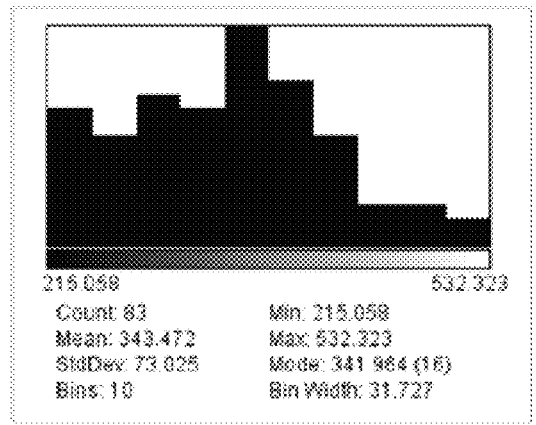
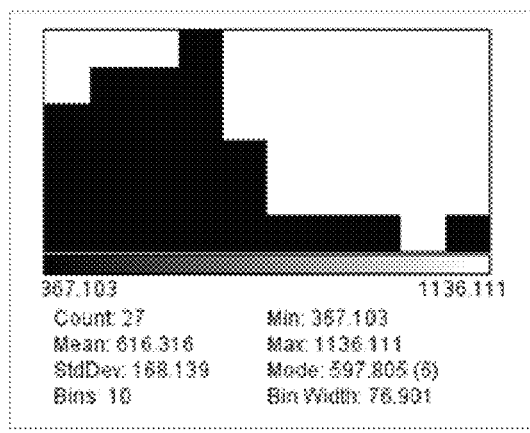
FIG. 9A  FIG. 9B

SENSORS FOR THE DETECTION OF ANALYTES

CROSS-REFERENCE TO A RELATED APPLICATION

This application claims the benefit of U.S. provisional application Ser. No. 62/292,919, filed Feb. 9, 2016, which is incorporated herein by reference in its entirety.

This invention was made with government support under contract number EEC-1160483 awarded by the National Science Foundation. The government has certain rights in the invention.

BACKGROUND OF INVENTION

Psychological stress is associated with increased risk of several health conditions including cardiovascular disease, autoimmune disorders, infectious disease, and mental illnesses (B. S. McEwen, Stress, adaptation, and disease. Allostasis and allostatic load, Ann. N. Y. Acad. Sci. 840 (1998) 33-44). The link between psychological stress and physical ailment can be seen in the biological responses associated with stress, namely the production of cortisol, a major glucocorticoid in humans.

Cortisol is synthesized and secreted by the zona fasciculata and the zona reticularis of the adrenal cortex. In its free form, cortisol plays an important role in the regulation of various factors such as, for example, blood pressure, glucose levels, and carbohydrate metabolism (R. Fraser, M. C. Ingram, N. H. Anderson, C. Morrison, E. Davies, J. M. C. Connell, Cortisol Effects on Body Mass, Blood Pressure, and Cholesterol in the General Population, Hypertension. 33 (1999) 1364-1368; D. S. Charney, Psychobiological Mechanism of Resilience and Vulnerability: Implications for Successful Adaptation to Extreme Stress, Am. J. Psychiatry. 161 (2004) 195-216). Cortisol levels can increase by ten-fold following surgery or other major trauma, as the steroid acts to prevent vascular collapse, reduce inflammation, and suppress immune response.

Additionally, cortisol, also referred to as hydrocortisone, is clinically used as a steroidal anti-inflammatory drug, and may be used in the treatment of, for example, acute inflammation, chronic inflammation, autoimmune diseases, allergic diseases, shock, gout, acute leukemia, and allograft rejection. However, chronically elevated cortisol is associated with the neuroendocrine causal pathway linking environmental or psychological distress to poor health outcomes (M. van Eck, H. Berkhof, N. Nicolson, J. Sulon, The effects of perceived stress, traits, mood states, and stressful daily events on salivary cortisol, Psychosom. Med. 58 447-58).

One of the major limitations of currently available cortisol immunoassay kits and immunosensors is their cross-reactivity and interference with the cortisol structural analogs, namely, progesterone and prednisolone (S. Tunn, G. Pappert, P. Willnow, M. Krieg, Multicentre evaluation of an enzyme-immunoassay for cortisol determination, Clin. Chem. Clin. Biochem. 28 (1990) 929-35; I. A. Ionita, D. M. Fast, F. Akhlaghi, Development of a sensitive and selective method for the quantitative analysis of cortisol, cortisone, prednisolone and prednisone in human plasma, J. Chromatogr. B. Analyt. Technol. Biomed. Life Sci. 877 (2009) 765-72). As recently reviewed by Krasowski et al., commercially available cortisol immunoassay kits still have cross-reactivity with the analogs, especially prednisolone (M. D. Krasowski, D. Drees, C. S. Morris, J. Maakestad, J. L. Blau, S. Ekins, Cross-reactivity of steroid hormone immunoassays: clinical significance and two-dimensional molecular similarity prediction, BMC Clin. Pathol. 14 (2014) 33). Additionally, conventional electrochemical biosensors suffer from low detection sensitivity that requires signal amplification for improved performance.

Sensors based on electrochemical processes can be used to detect a chemical or biological substance by using a transducing element to convert a detection event into a signal for processing and/or display. Biosensors employ biomolecules such as enzymes, antibodies, and nucleic acids as the sensing component. Alternatively, synthetic molecular biosensors can be configured to use specific chemical properties or molecular recognition mechanisms to identify target analytes. Biosensors can use the transducer element to transform a signal resulting from the detection of an analyte by the biologically sensitive component into a different signal that can be addressed by optical, electronic or other means.

Advantageously, electrochemical biosensors offer real-time sensing of clinically important biomolecules at low-cost and minimal power requirements ideal for decentralized point-of-care facilities and implantable or hand-held devices.

A biosensor typically comprises a bioreceptor and a signal transducer and is able to selectively sense the presence of a biological analyte of interest. Bioreceptors can be a variety of biological or chemical agents including, for example, nucleic acids, cells, antibodies, and enzymes. These bioreceptors can selectively react with, and bind to, a specific target analyte such as small chemical molecules, proteins, cells, DNA, and toxins. Conventional signal transducing methods employ various physical and chemical mechanisms, such as electrochemical, fluorescence, optics, and piezo-electricity.

The majority of currently-available biosensor techniques for the detection of target molecules rely on the use of natural antibodies and enzymes. Antibody-based biosensors possess a number of limitations such as inability for continuous monitoring, high cost of production, and need for special handling and storage, which altogether constitute roadblocks for commercialization of them as point-of-care diagnostic tools.

Therefore, there remains a need for developing sensitive biosensors for detecting and quantifying cortisol in a biological sample without requiring cumbersome handling and storage procedures.

BRIEF SUMMARY

The subject invention provides materials and methods for fabricating and using an electrochemical biosensor for detecting analytes. Advantageously, detection can be achieved without external labels/mediators. In preferred embodiments, a nanomaterial platform can be incorporated to the biosensor for enhanced detection sensitivity.

In a specific embodiment, the biosensor detects a given analyte when the analyte binds with a molecularly imprinted polymer (MIP) matrix immobilized atop a sensing electrode. Advantageously, the subject invention eliminates the need for a redox-probing agent commonly found in electrochemical biosensors. In some embodiments, the detection sensitivity of the biosensor is enhanced by modifying the electrode surface to comprise a plurality of nanoscopic metallic structures.

In preferred embodiments, the detection process is continuous, allowing the device to detect a given target analyte in different samples sequentially.

Advantageously, technologies provided herein can be used in a variety of low-power electronics for wearable applications.

In a specific embodiment, the present invention provides a device for detecting analytes, comprising at the surface of the sensing substrate a layer of conductive polymer matrix film, wherein the polymer matrix film is embedded with a plurality of molecular recognition sites congruent with the target analyte.

In some embodiments of the subject invention, the sensing substrate is the working electrode of a three-electrode cell that further comprises a counter electrode and a reference electrode.

In some embodiments, the polymer matrix is electrically conductive. In an exemplary embodiment the polymer matrix comprises polypyrrole.

In certain embodiments of the subject invention, the polymer matrix is molecularly imprinted by the target analyte as a template, which comprises characteristic molecular recognition sites created when the polymer polymerizes in the presence of the target analyte.

In some embodiments, the target analyte can be a biological or chemical substance including, but not limited to, a steroid hormone, protein, cell, toxin, or virus. In an exemplary embodiment, the target analyte is cortisol.

In some embodiments, the nanoscopic metallic structures can be nanowires, nanoparticles, or nanorods and comprise materials selected from, for example, silver, gold, platinum, palladium and copper.

In another aspect, the subject invention provides a method of fabricating a device for detecting a target analyte that comprises:

providing a conductive electrode;

depositing a layer of conductive polymer matrix film onto the surface of the electrode in the presence of the target analyte by electro-polymerization; and eluting the target analyte from the layer of polymer matrix film. In specific embodiments, the depositing of a plurality of nanoscopic metallic structures onto the conductive electrode comprises chemically treating the surface of the conductive electrode, and subsequently immersing the electrode in a salt solution of the metal from which the nanoscopic metallic structures are derived.

In some embodiments, the deposition of the layer of conductive polymer matrix film comprises electrochemically polymerizing monomers in the presence of the target analyte.

In a preferred embodiment, the elution of the target analyte from the polymer matrix comprises applying electrochemical overoxidation to the polymer matrix.

In an exemplary embodiment the conductive polymer matrix comprises polypyrrole.

In yet another aspect, the subject invention provides a method of detecting a target analyte using a sensing device, wherein the method comprises:

providing a biological sample, wherein the sample is a human physiological fluid selected from blood, plasma, serum, saliva, urine, mucous, and tears;

contacting the sample with an electrochemical sensing device, the device comprising a working electrode, a counter electrode, and a reference electrode, wherein the working electrode is a sensing substrate comprising at the surface a layer of conductive polymer matrix film and optionally a plurality of nanoscopic metallic structures, characterized in that the conductive polymer matrix film is embedded with a plurality of molecular recognition sites congruent with the target analyte;

applying voltage to the sensing device;

monitoring the current response of the device as the target analyte binds with the sensing substrate; and eluting any bound target analyte by electrochemically overoxidizing the sensing substrate.

The sample can be, for example, a human physiological fluid, a cell culture, food sample, or environmental samples. In preferred embodiments, the sample is a human physiological fluid selected from blood, plasma, serum, saliva, urine, mucous, and tears.

In some embodiments, the eluting of the target analyte comprises applying electrochemical overoxidation to the sensing device.

In certain embodiments, the detection process can be repeated immediately following the elution of the analyte from a previous sample and the application of a new sample placed in direct contact with the sensing device.

BRIEF DESCRIPTION OF THE DRAWINGS

FIG. 8C shows the molecular structure of cortisol and its structural analogs prednisolone, progesterone, and lactate.

FIGS. 9A-9D show polymer grain size distributions observed for PPy-SPCE, cortisol-PPy-SPCE, MIP-PPy-SPCE, and NIP-PPy-SPCE, respectively.

DETAILED DISCLOSURE

Figure 1:
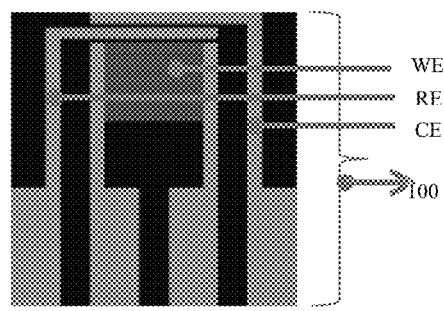
FIG. 1 shows an embodiment of a three-electrode cell as the sensing device.

The subject invention provides materials and methods for fabricating and using an electrochemical biosensor for detection of biological analytes. Advantageously, the sensing process can be carried out continuously.

In a specific embodiment, the biosensor detects an analyte when the analyte binds with a MIP-based matrix immobilized atop a sensing electrode. Advantageously, the devices and methods of the subject invention eliminate the need for a redox probing agent commonly found in electrochemical biosensors. Furthermore, in a preferred embodiment, the detection sensitivity of the biosensor is enhanced by modifying the surface of the electrode with a plurality of nanoscopic metallic structures. In a more preferred embodiment, the detection process is continuous, allowing the device to detect a given target analyte in different samples sequentially.

Advantageously, technologies provided herein can be used in a variety of low-power electronics for wearable applications.

In one aspect, the present invention provides a device for detecting biological analytes, comprising at the surface of the sensing substrate a layer of conductive polymer matrix film, wherein the polymer matrix film is embedded with a plurality of molecular recognition sites congruent with the target analyte.

The target analyte that can be detected using the technologies provided herein can be, for example, a steroid hormone, protein, cell, or virus. In an exemplary embodiment, the target analyte is cortisol.

In some embodiments of the subject invention, the sensing substrate is the working electrode of a three-electrode cell that further comprises a counter electrode and a reference electrode.

In specific embodiments of the subject invention, a target analyte is detected via a molecular recognition mechanism, evoking electrochemical signals that are then quantified by the sensor's circuit. Advantageously, in accordance with the subject invention, the electrochemical signals can be amplified by the plurality of nanoscopic metallic structures, thus greatly increasing the detection sensitivity of the device.

In some embodiments, the polymer matrix film is electrically conductive. Preferred embodiments provide that the polymer matrix film comprises polypyrrole.

Conductive polymers typically comprise aromatic hydrocarbons with conjugated π-bonds as the repeat unit. The majority of the known conductive polymers are 5- or 6-membered heterocycles with or without heteroatoms such as nitrogen, oxygen or sulfur. Conductive polymers are synthesized by polymerizing their respective monomer in the presence of electrochemical stimulation. In addition to polypyrrole (PPy), examples of conductive polymers include, but are not limited to, poly(fluorine), poly(phenylene), poly(acetylene), poly(aniline), poly(o-phenylenediamine), poly(thiophene), and poly(3,4-ethylenedioxythiophene). PPy is preferred due to its facile electropolymerization and stability in ambient conditions (B. L. Li, J. H. Luo, H. Q. Luo, N. B. Li, A novel strategy for selective determination of d-penicillamine based on molecularly imprinted polypyrrole electrode via the electrochemical oxidation with ferrocyanide, Sensors Actuators, B Chem. 186 (2013) 96-102; L. Özcan, Y. Sahin, Determination of paracetamol based on electropolymerized-molecularly imprinted polypyrrole modified pencil graphite electrode, Sensors Actuators, B Chem. 127 (2007) 362-369). Persons of ordinary skills in the art would recognize that other conductive polymers, now known or hereafter developed, may also be used to create the polymer matrix film provided herein.

The MIP provided herein can be a crosslinked polymeric network formed in the presence of an imprinting compound or "template molecule," such that the template molecule is later removed leaving a matrix that is able to recognize and bind to the template molecule via a complementary binding cavity. "Complementarity," as that term is used, herein indicates that the cavity left behind in the MIP matrix has a size matching the template molecule (e.g., cortisol), as well as binding sites that have affinity toward functional groups present in the template molecule such as, for example, keto and hydroxyl groups. The subject invention provides that the template molecule is the target analyte. The release or "elution" of the template molecule allows the MIP material to exhibit a selective "memory" with respect to the template molecule.

In some embodiments, the integration of MIP onto the sensing substrate's surface is accomplished via electropolymerization as it allows for the control of the thickness, morphology, and reproducibility of the MIP film by tuning experimental parameters such as, for example, the concentration of the target analyte and the monomer, polymerization cycles, and applied voltage (M. C. Blanco-López, S. Gutiérrez-Fernández, M. J. Lobo-Castañón, A. J. Miranda-Ordieres, P. Tuñón-Blanco, Electrochemical sensing with electrodes modified with molecularly imprinted polymer films, Anal. Bioanal. Chem. 378 (2004) 1922-8; N. Karimian, A. P. F. Turner, A. Tiwari, Electrochemical evaluation of troponin T imprinted polymer receptor, Biosens. Bioelectron. 59 (2014) 160-165). The thickness of the MIP film is an important factor that affects the film's recognition ability as well as the reproducibility of the sensor. The film thickness can be controlled by tuning the concentration of the monomers and the number of polymerization cycles.

The binding between the target analyte and the complementary molecularly cavity created by the MIP process is reversible, and the target analyte can be eluted from the polymer matrix. The template molecule scan be eluted or extracted from the MIP film using a number of methods. In preferred embodiments, the elution can be done using an appropriate solvent such as, for example, PBS, under the influence of electrochemical overoxidation. Other elution methods involving, for example, temperature, microwaves, and/or ultrasonics (to increase the rate of elution) resulted in distorted imprinted cavities and, consequently, made the MIP less efficient in rebinding and selectivity (R. A. Lorenzo, A. M. Carro, C. Alvarez-Lorenzo, A. Concheiro, To remove or not to remove? The challenge of extracting the template to make the cavities available in Molecularly Imprinted Polymers (MIPs), Int. J. Mol. Sci. 12 (2011) 4327-47).

Advantageously, the elution of bound target analyte molecules via overoxidation and the rebinding thereafter enables continuous monitoring of the cortisol level in a biological sample including, but not limited to, blood, serum, plasma, saliva, urine, mucous, and tears. In some embodiments, molecular imprinting technology combined with the sensing substrate can be used to recognize small molecules including, but not limited to, herbicides, metal ions, and amino acids.

In preferred embodiments, the sensing device can be used repeatedly such that following the detection of a target analyte in a first sample, the device can be used to examine a second sample for the same target analyte. In an exemplary embodiment, the same sensing device can be used repeatedly and continuously up to seven times for monitoring the concentration of cortisol.

In an exemplary embodiment, the sensing device provided herein can generate a response that varies linearly with the concentration of cortisol in the range of 1 pM to 10 μM ($R^2$=0.9925), with a detection limit of 1 pM. Furthermore, the same device can reused continuously for the detection of cortisol for up to seven times.

In some embodiments, the nanoscopic structures comprise a conductive metal, in elemental or alloy form, selected from silver, gold, platinum, palladium, copper, and combinations thereof. Non-limiting examples of the nanoscopic structures provided herein include nanoparticles, nanowires, and nanorods. Persons with ordinary skill in the art would readily recognize that other choices of materials and structures, now known or hereafter developed, may be used in forming the nanoscopic structures described herein.

The nanoscopic metallic structures provided herein should offer high capture efficiency, fast response time due to large adsorption surface (surface-to-volume ratio>1000 $m^2/g$), high electrical conductivity, and short diffusion time. Additionally, they should not be easily reduced or oxidized over a range of potentials. Moreover, these structures promote electron transfer and demonstrate catalytic activity for many electrochemical reactions. Advantageously, metallic structures are easily detectable using voltammetry as it gives reversible redox peaks when an appropriate potential is applied, and the size similarity between the nanowires and the redox enzymes can be used effectively for developing a highly sensitive biosensor.

In another aspect, the subject invention provides a method for fabricating a device for detecting a target analyte that comprises:
  providing a conductive electrode;
  depositing a layer of conductive polymer matrix film onto the surface of the electrode in the presence of the target analyte by electrochemical polymerization; and
  eluting the target analyte from the layer of polymer matrix film. In some embodiments of the subject invention, the modified conductive electrode (i.e., the sensing substrate) is the working electrode of a three-electrode cell that further comprises a counter electrode and a reference electrode.

In some embodiments, the method further comprises depositing a plurality of metallic nanoscopic structures onto the surface of the conductive electrode prior to the electrochemical polymerization, wherein the nanoscopic structures are selected from nanowires, nanoparticles, and nanorods, comprising materials selected from silver, gold, platinum, palladium, and copper.

The nanoscopic metallic structures can be deposited onto the surface of the conductive electrode by a number of methods including, but not limited to, electrodeposition, atomic layer deposition, and sputtering. In specific embodiments, the depositing of a plurality of nanoscopic metallic structures onto the base electrode comprises chemically treating the surface of the base electrode, and immersing the electrode in a salt solution of metallic ions from which the nanoscopic metallic structures are derived.

In some embodiments, the deposition of the layer of conductive polymer matrix film comprises electropolymerizing monomers in the presence of a target analyte. In some embodiments, the electropolymerization is accomplished via applying multiple cycles of potential to the mixture of the monomers and the target analyte. Advantageously, by controlling the concentration of the monomer, the target analyte, and the duration and the magnitude of the potential cycles, the thickness of the layer of conductive polymer matrix can be regulated.

In an exemplary embodiment, the target analyte is cortisol. Other non-limiting examples of target analytes are steroid hormones (e.g., progesterone, testosterone, estradiol, and aldosterone), amino acids (e.g., tyrosine, cysteine, glutamine, and phenylalanine), small molecules with MW less than 875 Da (e.g., lactate and glucose), proteins, cells, toxins, and viruses.

The elution of the target molecule from the polymer matrix to create specific recognition sites can be done by a number of methods including, but not limited to, washing, sonicating, and electrochemical overoxidation. In preferred embodiments, the elution of the target analyte from the polymer matrix film comprises applying electrochemical overoxidation to the polymer matrix.

In an exemplary embodiment, the conductive polymer matrix comprises polypyrrole.

In yet another aspect, the subject invention provides a method of detecting a target analyte using a sensing device, comprising:
  providing a biological sample, wherein the sample is a human physiological fluid selected from blood, plasma, serum, saliva, urine, mucous, and tears;
  contacting the sample with an electrochemical sensing device, the device comprising a working electrode, a counter electrode, and a reference electrode, wherein the working electrode is a sensing substrate comprising at the surface a layer of conductive polymer matrix film and optionally a plurality of nanoscopic metallic structures, characterized in that the conductive polymer matrix film is embedded with a plurality of molecular recognition sites congruent with the target analyte;
  applying voltage to the sensing device;
  monitoring the current response of the device as the target analyte binds with the sensing substrate; and
  eluting any bound target analyte by electrochemically overoxidizing the sensing substrate.

The sample can be, for example, a physiological fluid, cell culture, tissues, food sample, or an environmental sample. The sample can be from a plant or an animal. The animal can be, for example, a human. In preferred embodiments, the sample is a human physiological fluid selected from blood, plasma, serum, saliva, urine, mucous, and tears.

In some embodiments, the eluting of the target analyte comprises applying electrochemical overoxidation to the sensing device.

In some embodiments, immediately following the elution of the target analyte from a first sample, a second sample can be contacted with the sensing device to continue the detection process of the same target analyte.

In some embodiments, an array of sensing devices comprising the same or different sensing materials are exposed to the same target analyte simultaneously to improve signal identification.

As an advantage over conventional antibody-based electrochemical sensing devices that are disposable and require refrigerated storage, the device provided herein can be used repeatedly to detect a target analyte of interest at room temperature and remain usable for a prolonged period of time.

In an exemplary embodiment, the device showed good reusability with sensitivity that remained above about 90% after 6 cycles of elution and rebinding, while the sensitivity only decrease by about 10% after 4 weeks of storage at room temperature.

Other objects, features, and advantages of the invention will be apparent to those skilled in the art from the detailed description of the invention which will now follow, taken in conjunction with the tables, drawings, and the accompanying claims.

EXAMPLES

The following are examples that illustrate the aforementioned embodiments and should not be construed as limiting.

Pyrrole monomer (≥98%), potassium ferricyanide ($K_3[Fe(CN)_6]$), potassium ferrocyanide ($K_4[Fe(CN)_6]$), and potassium chloride (KCl) were purchased from Sigma-Aldrich Co., USA. Phosphate-buffered saline (PBS) (10 mM, pH 7.4) was prepared by dissolving a PBS tablet (2005.5 mg) in 200 mL of deionized (DI) water. Stock solution of cortisol was prepared by dissolving 1 mg of cortisol in 1 mL of ethanol. Cortisol working aliquots were prepared by diluting the stock solution with PBS. Standard stock solution of $K_3[Fe(CN)_6]/K_4[Fe(CN)_6]$ (5 mM) was prepared using PBS. A cortisol enzyme immunoassay kit was procured from Arbor Assays, Mich., and the recommended protocol was adapted to detect salivary cortisol. 50 µL of 4× diluted saliva was used for the detection of cortisol.

All electrochemical experiments were performed with an Autolab Potentiostat/Galvanostat (Eco Chemie, Netherlands). A planar screen-printed carbon electrode (SPCE) consisting of a carbon working electrode, a carbon counter electrode, and an Ag/AgCl reference electrode (CH Instruments, Inc., USA) were used to design the three-electrode cortisol MIP sensor. Scanning electron microscopic images (SEM) of the imprinted films were taken using a Jeol (JSM-7000) electron microscope.

Example 1—Electrochemical Deposition

The electrochemical deposition of silver nanowires onto a working electrode was performed. Prior to the deposition, the electrode was cleaned and pretreated to remove any contaminants and to increase surface roughness. Then, the pretreated electrode was immersed in 0.1 M of $KNO_3$ solution comprising 5.0 mM of $AgNO_3$ and electrodeposited for different durations of time to obtain the silver nanowires modified electrode.

Example 2—Electropolymerization of MIP

Following the deposition of silver nanowires, the electropolymerization of MIP conducting film was performed using cyclic voltammetry. Cortisol-embedded polypyrrole atop the electrode was fabricated by sweeping the voltage range between 0 V and 0.9 V vs Ag/AgCl at a scan rate of 50 mV/s for 10 complete cycles in 0.1 M of phosphate buffer solution (PBS) comprising 0.4 M of pyrrole and 0.1 M of KCl. 0.1 M cortisol was added in the solution as the template molecule before electropolymerization.

Example 3—Electrochemical Overoxidation of the Polymer Matrix

After the electropolymerization, the cortisol-embedded polypyrrole was overoxidized in 0.1 M PBS by scanning the potential from 0.6 to 1.6 V for 50 complete cycles to remove the imprinting cortisol molecules.

A control electrode modified with non-imprinted polymer (NIP) was obtained in the same way, but without cortisol being added as a template. Modified electrodes were dried under a nitrogen flow and stored at room temperature.

Figure 2:
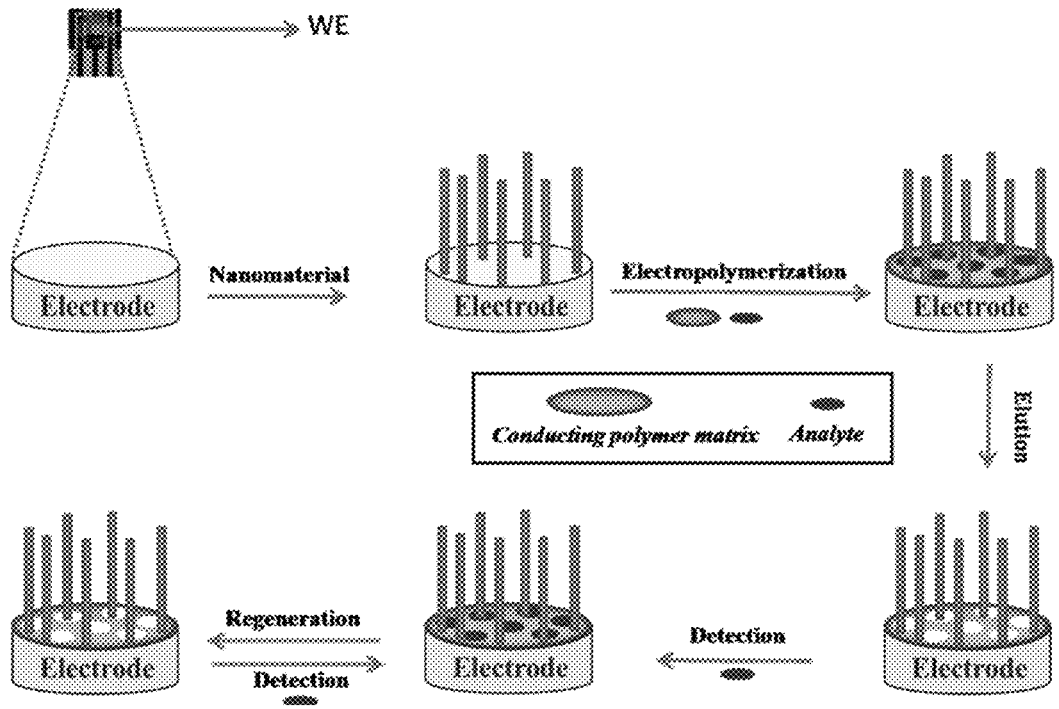
FIG. 2 shows an embodiment of the fabrication and use of an MIP-based sensor modified with nanoscopic metallic structures.

The stepwise fabrication of the biosensor is illustrated in FIG. 2. The sensor thus created comprised specific recognition cites for cortisol and can be used for detection of cortisol without using any redox mediator.

Example 4—Electropolymerization of MIP on SPCE

The screen-printed carbon electrode (SPCE) was pretreated by cycling the potential between −1.5 V to 1.5 V at a scan rate of 100 mV/s in 0.1 M $H_2SO_4$ for 10 cycles. The SPCE was then washed with deionized water and dried at room temperature. The electrosynthesis of MIP films was performed using cyclic voltammetry by cycling the potential range from 0 V to 0.9 V at a scan rate of 50 mV/s for 10 cycles in PBS (10 mM, pH 7.4) comprising 0.8 M pyrrole and 0.1 M KCl (M. Pandiaraj, T. Madasamy, P. N. Gollavilli, M. Balamurugan, S. Kotamraju, V. K. Rao, et al., Nanomaterial-based electrochemical biosensors for cytochrome using cytochrome reductase, Bioelectrochemistry. 91 (2013) 1-7). 10 mM cortisol was added to the solution before the polymerization. As the monomers polymerize, cortisol molecules migrate towards the working electrode and are entrapped in the polymer matrix.

Figure 3:
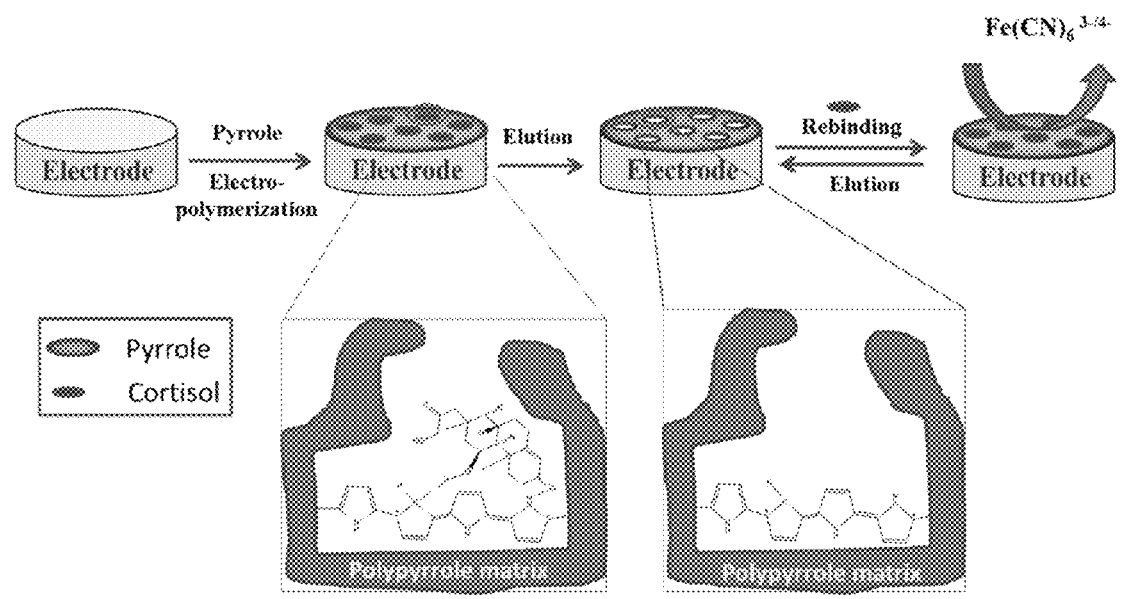
FIG. 3 is a schematic representation of the stepwise fabrication of an exemplary cortisol MIP biosensor.

After polymerization, the entrapped cortisol molecules were extracted from the conducting polymer matrix to produce a surface with cavities that are complementary in shape and functionality to cortisol. Cortisol templates were extracted through the over-oxidation of the PPy by cycling the potential range between −0.2 and 0.8 V for 25 cycles in PBS. The same procedure (polymerization followed by overoxidation) was used to fabricate NIP electrodes but without the cortisol template. MIP and NIP modified electrodes were then dried under nitrogen flow and stored at room temperature. The stepwise fabrication of the cortisol imprinted sensor is illustrated in FIG. 3.

The electrochemical detection of cortisol by the MIP sensor was performed by placing 5 µL of appropriate concentration of cortisol solution at the working electrode for 10 min. The electrochemical measurements were carried out in the presence of 40 µL of 5 mM $K_3[Fe(CN)_6]/K_4[Fe(CN)_6]$ solution in PBS (10 mM, pH 7.4) at room temperature.

Example 5—Confirmation of Binding of Cortisol with the MIP

Figure 4A:
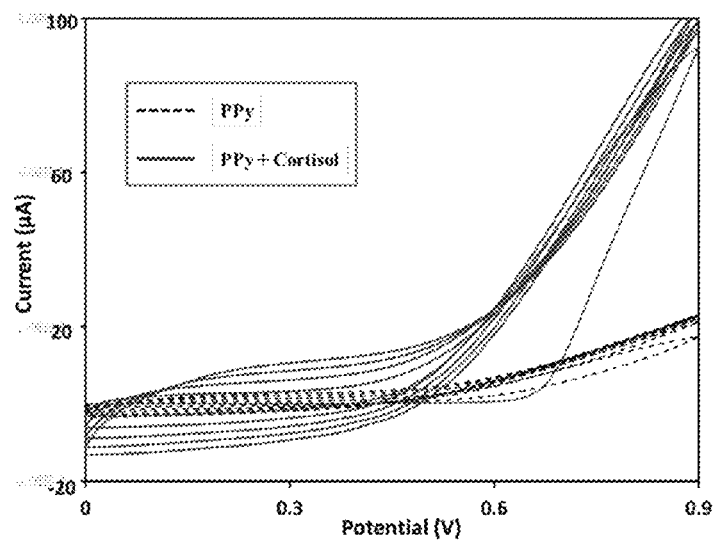
FIG. 4A shows cyclic voltammograms (CV) taken during the electropolymerization of pyrrole onto the screen-printed carbon electrode (SPCE) with (solid lines) and without (dotted lines) the presence of 10 mM cortisol. Scan rate: 50 mV/s.

Formation of cortisol-specific MIP films on the electrode surface was achieved by electrochemical polymerization of PPy in the presence of cortisol. The polymer growth was monitored via changes in the voltammograms obtained during the electropolymerization process. The voltammograms obtained during the electropolymerization of pyrrole in the absence (dotted lines) and in the presence of cortisol (solid lines) from 0 V to 0.9 V at 50 mV/s using 0.1 M KCl as a supporting electrolyte are shown in FIG. 4A. In both cases, the oxidation currents were observed to increase at each scan cycle, implying a controlled growth of the polymer. This suggests that the thickness of the polymer film can be controlled by regulating the scan cycles.

During polymerization, cortisol molecules diffuse towards the electrode and bind to the PPy matrix through hydrogen bonding (FIG. 3). Although the two voltammograms are similar in shape as shown in FIG. 4A, the capacitive currents observed for the electropolymerization in the presence of cortisol (solid lines) is significantly higher than those obtained in its absence (dotted lines). The increased capacitive current of polymer film in the presence of cortisol confirms the binding of cortisol, an electro-inactive molecule, with the polymer.

Example 6—Removal of Cortisol Templates

Removal of cortisol templates from the polymeric matrix was used to form complementary imprinted sites for the subsequent rebinding.

Figure 4B:
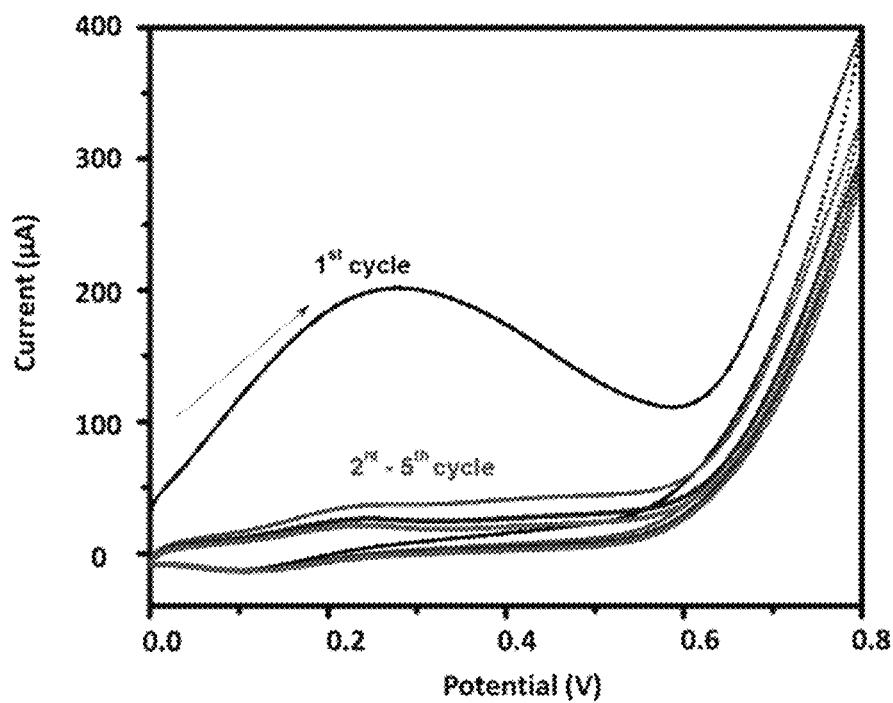
FIG. 4B shows recorded voltammograms during the elution of cortisol from the PPy matrix in PBS (10 mM, pH 7.4). Scan rate of 50 mV/s.

Electrochemical overoxidation process was used to remove cortisol molecules from the PPy matrix. The PPy was overoxidized by scanning the potential in a range of −0.2 V to +0.8 V for 25 cycles in PBS at a scan rate of 50 mV/s (FIG. 4B). For clarity, the initial five scans are shown in FIG. 4B. During the elution scans, a broad irreversible voltammetric peak was observed at ~0.3 V, which was due to the overoxidation of PPy (Y. Li, R. Qian, Electrochemical overoxidation of conducting polypyrrole nitrate film in aqueous solutions, Electrochim. Acta. 45 (2000) 1727-1731). As can be seen in FIG. 4B, no cathodic peak can be observed on the reverse scan, which indicates that the overoxidation of PPy is electrochemically irreversible.

The electrochemical overoxidation causes the removal of cortisol from the PPy matrix while oxygen-containing groups, such as carboxyls, are inserted into the backbone of the polymer. The decrease in the current response during subsequent scan cycles is due to a decrease in conductivity of the PPy film as a result of overoxidation. Since overoxidation was performed here under neutral pH conditions, the degradation of the PPy matrix was avoided.

The NIP fabrication process follows the same protocol used to fabricate MIP (polymerization followed by overoxidation), but without cortisol as a template.

Example 7—Electrochemical Behavior of Cortisol MIP Sensor

The electrochemical behavior of the stepwise fabrication of the cortisol MIP sensor was studied in 5 mM $K_4[Fe(CN)_6]/K_3[Fe(CN)_6]$ solution comprising PBS. The results are shown in FIG. 5.

The CVs of $[Fe(CN)_6]^{3-}/[Fe(CN)_6]^{4-}$ redox probe was chosen as a marker to investigate the changes in the electrode behavior after each step of sensor assembly. As shown in FIG. 5 curve a, two well-defined reversible redox peaks for the $[Fe(CN)_6]^{3-}/[Fe(CN)_6]^{4-}$ redox couple are observed with bare SPCE. The PPy-modified SPCE showed an obvious increase in the peak current for the redox probe along with an increase in capacitive currents (FIG. 5 curve b). This was attributed to the increase in effective surface area by the conducting PPy matrix on the SPCE surface. The permeability of the porous PPy film was also responsible for the increased electron transport kinetics. Because $[Fe(CN)_6]^{3-}/[Fe(CN)_6]^{4-}$ is an anion and due to electrostatic interactions, the $[Fe(CN)_6]^{3-}/[Fe(CN)_6]^{4-}$ ions insert easily into the positively charged PPy film and are thus involved in rapid electron transfer kinetics.

Figure 5:
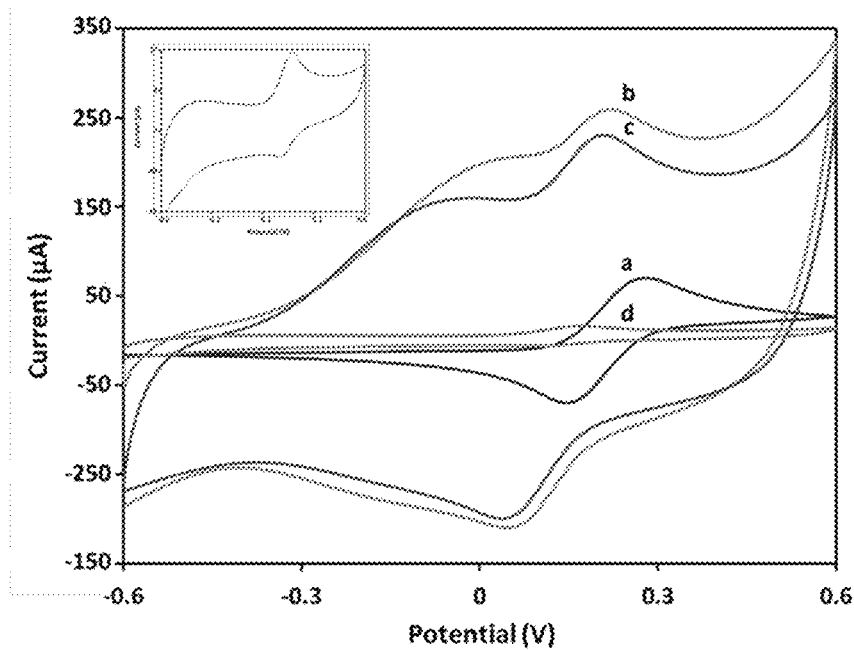
FIG. 5 shows cyclic voltammograms of 5 mM $K_4[Fe(CN)_6]/K_3[Fe(CN)_6]$ solution on (a) bare SPCE, (b) PPy-SPCE, (c) cortsiol-PPy-SPCE, and (d) MIP-PPy-SPCE. Scan rate: 50 $mVs^{-1}$. The inset is an enlarged version of curve (d).

The peak current response observed for the cortisol bound PPy matrix (FIG. 5 curve c) was much lower than the one observed for the PPy matrix without cortisol (FIG. 5 curve b). This further confirms that cortisol was effectively loaded onto the PPy matrix and hinders the electrochemical response of $[Fe(CN)_6]^{3-}/[Fe(CN)_6]^{4-}$.

It should be noted that the removal of cortisol from the PPy matrix drastically decreases the current response (FIG. 5 curve d). The voltage-induced overoxidation makes the PPy insulated by introducing carbonyl and carboxyl groups in the polymer backbone. The inset of FIG. 5 depicts the enlarged version of curve d, showing the redox currents observed with the overoxidized PPy matrix.

Example 8—Surface Morphology of MIP and NIP

Figure 6A:
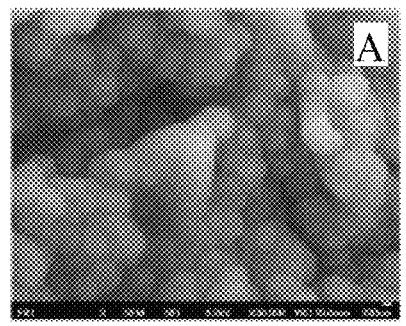
FIGS. 6A-6D are SEM images of PPy-SPCE, cortisol-PPy-SPCE, MIP-PPy-SPCE, and NIP-PPy-SPCE, respectively.
Figure 6B:
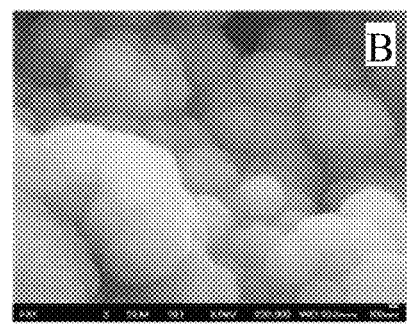
Figure 6C:
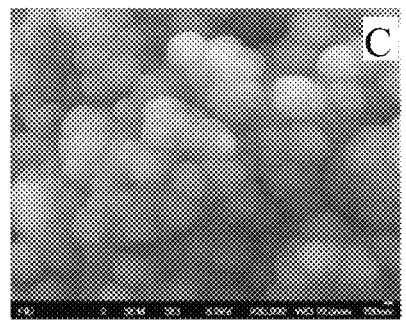
Figure 6D:
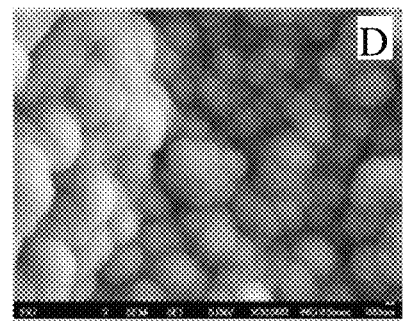

Surface morphologies of MIP and NIP modified electrodes were obtained at 30,000× magnification and are shown in FIGS. 6A-6D. FIG. 6A depicts the SEM image of PPy deposited SPCE. After electro-polymerization, the surface of the SPCE was coated with micro-porous PPy matrix creating a cauliflower-like structure constituted by microspherical grains. The average diameter of the grain was 343.47 nm. When pyrrole was polymerized in the presence of cortisol, an increase in grain size was observed (FIG. 6B). The average diameter of the grains increased to 616.32 nm, suggesting the incorporation of cortisol molecules into the polymer matrix. Overoxidation of PPy matrix resulted in decreased grain size with increased porosity due to the removal of cortisol from the matrix (FIG. 6C). The average diameter of the grain size was 342.83 nm. For comparison, the SEM image of NIP modified electrode is given in FIG. 6D. As can be seen from the SEM images, the surface of the MIP modified electrode is rough due to imprinted cavities of cortisol, whereas the surface of the NIP modified electrode is smooth without the imprinting cavities. The grain size distribution observed for MIP and NIP modified electrodes were shown in FIGS. 9A-9D.

Figure 7A:
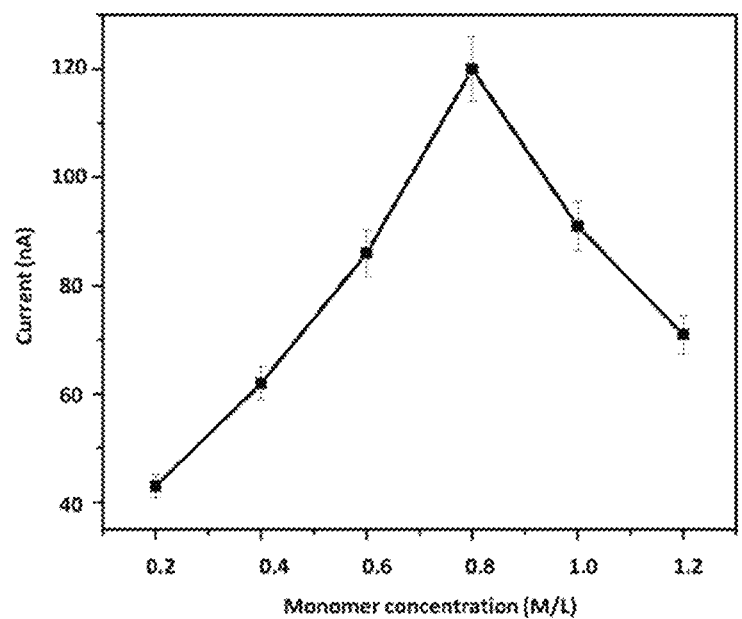
FIG. 7A shows the effect of the monomer concentrations on the response of the sensor to cortisol.

Example 9—the Effect of Monomer Concentrations on the Electrochemical Response of the MIP Sensor To investigate the effect of monomer concentrations on the electrochemical response of the MIP sensor, the cortisol MIP electrodes were prepared in solutions with a constant concentration of cortisol (10 mM) and varying concentrations of pyrrole (from 0.2 M to 1.2 M) (FIG. 7A). The polymerization and elution procedure to form MIP electrodes was followed as described herein.

The fabricated cortisol MIP electrodes were characterized using cyclic voltammetry in 5 mM $K_4[Fe(CN)_6]/K_3[Fe(CN)_6]$ solution containing PBS. The current response of the $[Fe(CN)_6]^{3-}/[Fe(CN)_6]^{4-}$ redox probe increased with increasing monomer concentration and reached a maximum value at 0.8 M, after which the current response decreased with further increases in the concentration of pyrrole monomer. This behavior can be attributed to the formation of a very thick layer of MIP at higher concentrations of monomer, which in turn affected the electron transfer of the $[Fe(CN)_6]^{3-}/[Fe(CN)_6]^{4-}$ redox couple.

Thus, the optimized 0.8 M pyrrole monomer concentration was chosen for the electrochemical polymerization to obtain the highest sensitivity for the determination of cortisol.

Example 10—Optimization of Scan Cycles

Since the thickness of the polymer matrix can also be tuned via controlling the number of electro-polymerization cycles, the number of scan cycles used for MIP synthesis was optimized. A series of MIP electrodes was fabricated by following the experimental procedures provided herein;

however, a different number of polymerization cycles was used to determine the optimal thickness. The electrochemical elution of the cortisol template from the polymeric matrix was performed using cyclic voltammetry as detailed herein.

Figure 7B:
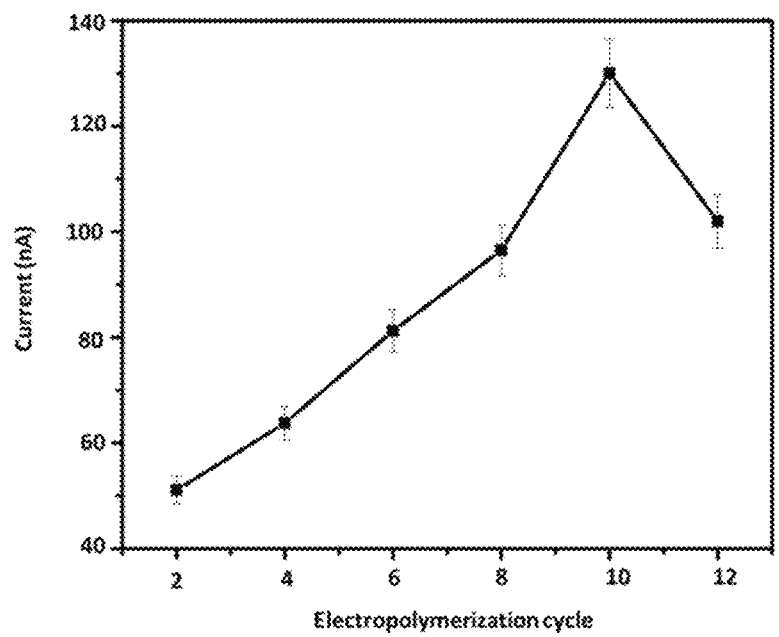
FIG. 7B shows the effect of the different cycles of the electropolymerization of MIP.

As shown in FIG. 7B, the current response of the redox probe $[Fe(CN)_6]^{3-}/[Fe(CN)_6]^{4-}$ reached a maximum after the $10^{th}$ cycle of polymerization, and then decreased as the number of polymerization cycles increased. MIP films that were formed with less than 10 scan cycles were found to be thin and less stable at the working electrode, whereas films formed with greater than 10 cycles formed thicker sensing layers that hinder the electron transfer of $[Fe(CN)_6]^{3-}/[Fe(CN)_6]^{4-}$ redox probe.

These results indicated that 10 is the optimum number of polymerization cycles.

Example 11—Removal of the Target Molecules Form the MIP

The efficient and controlled removal of the target molecules from the polymeric matrix is essential to fabricating reproducible MIP biosensors. An effective method is needed to regenerate the imprinting sites after the binding events to make the MIP sensors reusable. In this study, to create imprinting sites, the controlled removal of template molecules was performed by voltage-induced overoxidation. The electrochemical elution of the cortisol template from the polymeric matrix was performed using cyclic voltammetry as detailed herein.

Figure 7C:
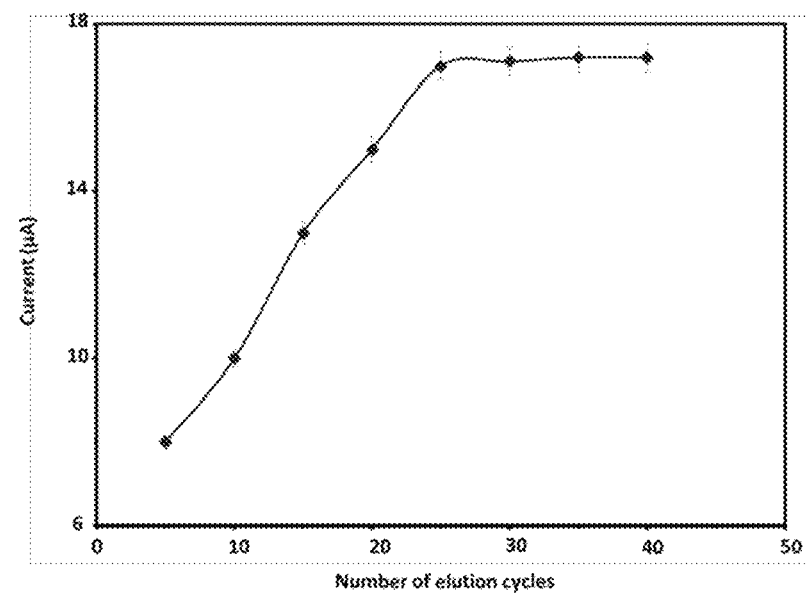
FIG. 7C shows the effect of electrochemical extraction cycles on the current response.

In order to optimize the number of extraction cycles, varying numbers of extraction cycles (5-40) were performed on the cortisol embedded PPy-SPCE. The MIP sensors were characterized after each cycle of target removal, using the redox probe $[Fe(CN)_6]^{3-}/[Fe(CN)_6]^{4-}$ As the number of elution cycles increased, the current response of the MIP sensor also increased, indicating the controlled release of cortisol molecules. The maximum current response of the electrode was obtained at the $25^{th}$ cycle (FIG. 7C). Thus, the extraction cycles were optimal at the $25^{th}$ iteration for complete extraction of the template from the polymeric matrix.

Figure 10:
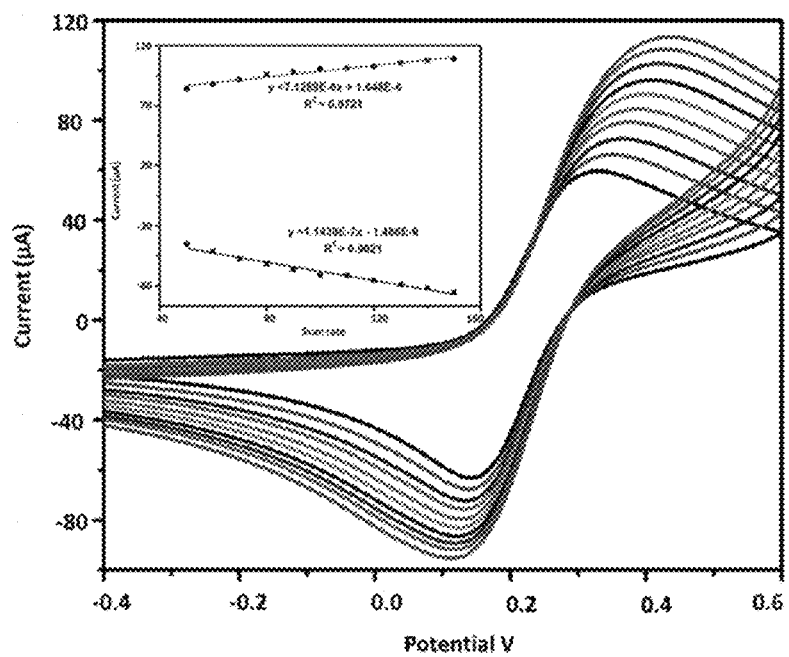
FIG. 10 shows the results of CV studies of the cortisol MIP sensor as a function of scan rate (50-150 mV/s). The inset shows the magnitude of current response vs. scan rate.

Typical CV curves generated by the cortisol MIP sensor in $[Fe(CN)_6]^{3-}/[Fe(CN)_6]^{4-}$ redox probe at different scan rates ranging from 50 to 150 50 mV/s were studied and shown in FIG. 10. As observed in FIG. 10, both the cathodic and anodic peak currents increased with an increase in scan rate from 50 to 150 mV/s. The anodic and cathodic peak currents are both linearly proportional to the square root of the relevant scan rate, suggesting a diffusion controlled behavior with an electron transfer process (Bard, Allen J. LRF (2000) Electrochemical Methods: Fundamentals and Applications. Wiley; $2^{nd}$ edition).

Figure 11:
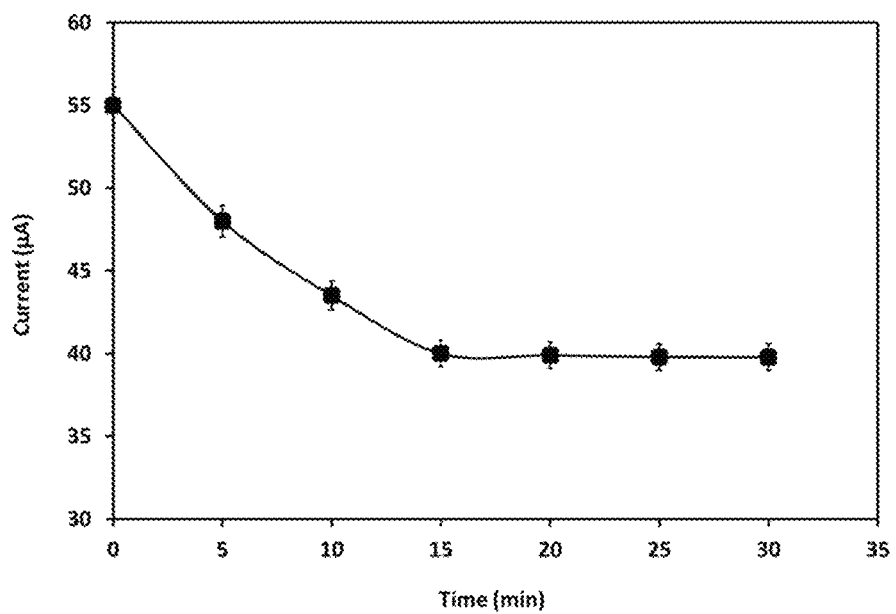
FIG. 11 shows the effect of incubation time on the current response of the cortisol MIP sensor.

The effects of incubation time on the performance of the cortisol MIP sensor was also investigated (FIG. 11). After the extraction of cortisol, the MIP sensors were left in contact with a standard solution of 10 pM cortisol for different incubation times (0-30 min). With increasing incubation time, the current responses of the $[Fe(CN)_6]^{3-}/[Fe(CN)_6]^{4-}$ redox probe decreased and then stabilized when the incubation time was longer than 15 min. Thus, an incubation time of 15 min was adopted in the subsequent work.

In order to evaluate the influence of the pH on the performance of the cortisol MIP sensor, the sensor was tested with a series of PBS with different pH, ranging from 5.8 to 7.8. The experimental results showed that an increase in pH from 5.8 to 7.4 resulted in an increased peak current of $[Fe(CN)_6]^{3-}/[Fe(CN)_6]^{4-}$ redox probe; further increase in pH resulted in decrease in peak current. The results showed that the maximum current response occurred at pH 7.4. The optimum pH 7.4 was hence chosen for all the experiments.

Example 12—Detection of Cortisol Using the MIP Sensor

Figure 8A:
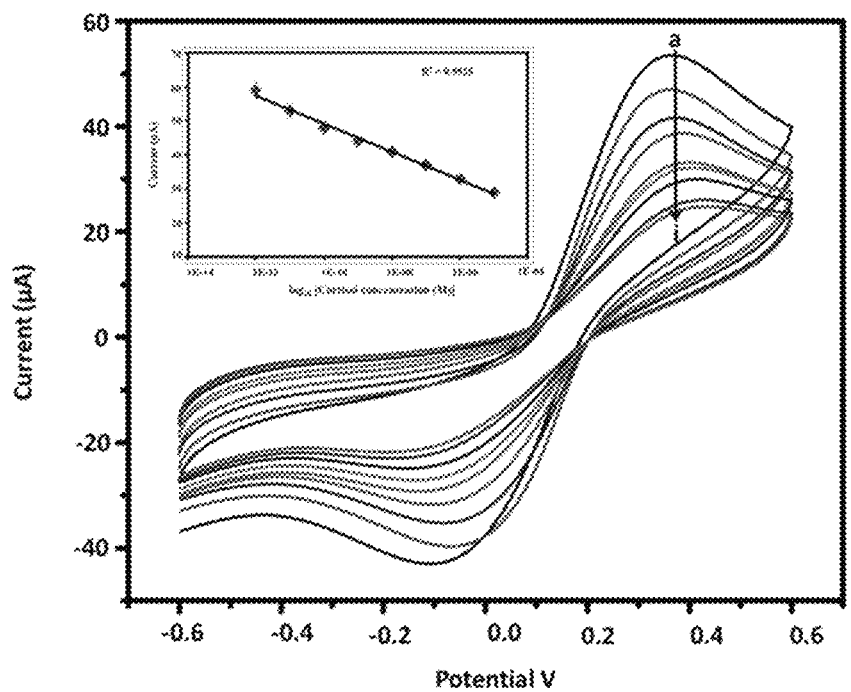
FIG. 8A shows the electrochemical response of MIP-PPy-SPCE as a function of cortisol concentration (1 pM to 10 uM) using 5 mM $K_4[Fe(CN)_6]/K_3[Fe(CN)_6]$ solution. The inset shows the calibration curve between magnitudes of response current and logarithm of cortisol concentrations.

Typical CV scans obtained for several concentrations of cortisol in PBS containing 5 mM $[Fe(CN)_6]^{3-}/[Fe(CN)_6]^{4-}$ using the cortisol MIP sensor at 50 mV/s are shown in FIG. 8A. The figure depicts the magnitude of the electrochemical current response, which decreases as a function of increasing cortisol concentration when incubated for 15 min. Decreases in current response are attributed to the binding of cortisol molecules to the MIP sites that hinder electron transport of $[Fe(CN)_6]^{3-}/[Fe(CN)_6]^{4-}$ redox probe.

A calibration curve between the magnitudes of current response and the logarithm of cortisol concentration has been plotted (inset, FIG. 8A). The cathodic peak current observed at −0.35 V was used to plot calibration curves. The current responses to cortisol obtained with the MIP sensor were linear from 1 pM to 10 μM ($R^2$=0.9925), with a detection limit of 1 pM.

Example 13—Selectivity

Figure 8B:
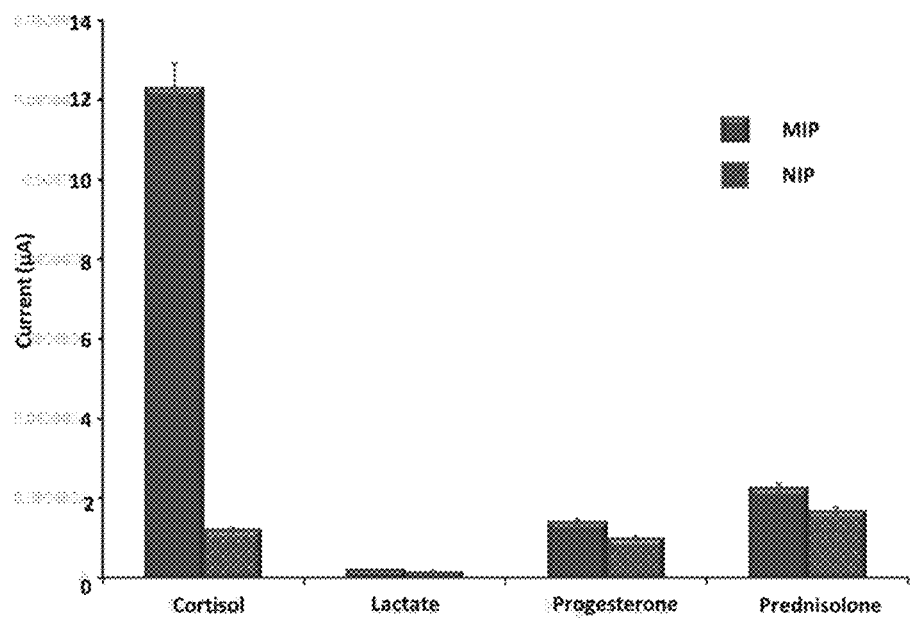
FIG. 8B shows the change in peak current values observed at cortisol MIP (blue) and NIP (red) electrode in the presence of cortisol and other interferents individually each at 100 nM.
Figure 9C:
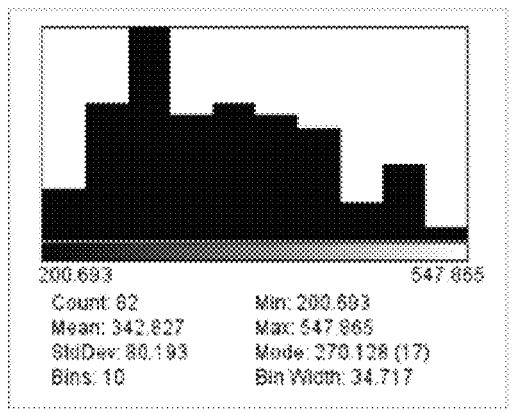
Figure 9D:
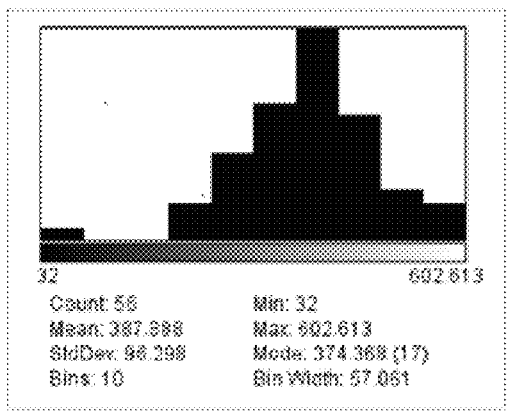

The selectivity assay for cortisol MIP sensor was carried out using three interfering analytes: progesterone, prednisolone, and lactate. The change in peak current values observed at MIP and NIP electrodes in the presence of cortisol and other interferents, each at 100 nM, are shown in FIG. 8B. The imprinting factor (β), a measure of the strength of interaction between the target molecule and MIP sensor, was calculated according to the following equation, where $I_{pa}$ is the cathodic peak current:

$$\beta = \frac{I_{pa}(MIP\ sensor)}{I_{pa}(NIP\ sensor)}$$

The values of β were 10.25, 1.27, 1.41, and 1.33 for cortisol, lactate, progesterone, and prednisolone, respectively. Based on the values obtained, it is clear that the MIP sensor showed higher binding capability towards cortisol (maximum β value) than the other interferents.

The above results revealed that the MIP sensor exhibited higher recognition selectivity toward cortisol.

The cross-reactivity percentage was also calculated using the current values. It showed that lactate has very negligible interference (1.5%) while progesterone (11.4%) and prednisolone (18.3%) have slightly higher cross-reactivity with cortisol detection.

The chemical structures of cortisol and other interferents are shown in FIG. 8C. Prednisolone and progesterone have chemical structures very similar to cortisol and thus interfere with cortisol measurement. But the percentage of cross-reactivity of the present MIP sensors is much lower than the conventional immunoassay.

Example 14—Reproducibility

To investigate the reproducibility, five sensors were freshly prepared and used to detect the same concentration of cortisol (100 nM). Based on the current responses obtained, the relative standard deviation (RSD) was calculated to be 4.16%, confirming that the sensor has good reproducibility (Table 1). The RSD was determined by five successive measurements of a 100 nM cortisol solution using the same cortisol MIP electrode (i.e., used each time after elution process) and was estimated to be 4.81% (Table 2). After the binding event, sensors were regenerated by electrochemical elution and were reused to detect cortisol.

The experimental results demonstrated that the cortisol MIP sensor could be used continuously for seven times; after that, the adhesion of the polymer to the electrode weakens. The stability of the sensor was examined by monitoring the current response for a 10 nM cortisol solution at regular intervals of 2 days for a period of four weeks. After four weeks, the sensor retained 90% of its current response. This suggests that the proposed sensor has acceptable storage stability.

TABLE 1

Reproducibility experiments of the MIP-PPy-SPCE sensor

| | Cortisol MIP sensors | | | | | |
|---|---|---|---|---|---|---|
| | 1 | 2 | 3 | 4 | 5 | RSD |
| Current$^a$ (µA) | 30.11 | 29.61 | 28.24 | 30.39 | 28.59 | 4.16% |

$^a$Average of three experimental results

TABLE 2

Repeatability experiments of the cortisol MIP-PPy-SPCE sensor

| | Cortisol solutions | | | | | |
|---|---|---|---|---|---|---|
| | 1 | 2 | 3 | 4 | 5 | RSD |
| Current$^a$ (µA) | 28.15 | 29.10 | 29.85 | 30.98 | 31.80 | 4.81% |

$^a$Average of three experimental results

Example 15—Clinical Use

To further investigate the feasibility of the newly developed cortisol MIP sensor for usage in clinical analyses, salivary cortisol concentrations of farmworkers were tested using the MIP sensor and reference ELISA.

The protocol to detect cortisol using the sensor and ELISA was adopted from our previous work (S. K. Pasha, a. Kaushik, a. Vasudev, S. a. Snipes, S. Bhansali, Electrochemical Immunosensing of Saliva Cortisol, J. Electrochem. Soc. 161 (2013) B3077-B3082). In short, 5 µL of each saliva sample was incubated on the biosensor for 15 min to ensure proper binding, followed by a wash using PBS (10 mM, pH 7.4) to remove any unbound saliva. Next, cyclic voltammetry scans were recorded in 5 mM $K_4[Fe(CN)_6]/K_3[Fe(CN)_6]$ solution containing PBS.

The results obtained using the MIP cortisol sensors are comparable to the results obtained with ELISA (Table 3). It was observed that a factor of 2.4 was applied to all the CV calculations in comparison to ELISA. These results confirm the suitability of the electrode for human sample applications.

TABLE 3

Comparison of saliva cortisol estimated using ELISA and cortisol MIP sensor.

| Saliva samples | Salivary Cortisol (ELISA) (µg/dL) | Salivary Cortisol (MIP sensor) (nM/L) |
|---|---|---|
| Sample 1 | 0.237 | 6.75 |
| Sample 2 | 0.155 | 4.32 |
| Sample 3 | 0.144 | 4.13 |
| Sample 4 | 0.072 | 2.16 |

The examples and embodiments described herein are for illustrative purposes only and various modifications or changes in light thereof will be apparent to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

N. Karimian et al., An ultrasensitive molecularly-imprinted human cardiac troponin sensor. *Biosensors and Bioelectronics*, 50, 492 (2013).

I. Chianella et al., Direct replacement of antibodies with molecularly imprinted polymer nanoparticles in ELISA-development of a novel assay for vancomycin. *Analytical Chemistry*, 85, 8462, 2013.

Z. Liu et al., Single nanoporous gold nanowire sensors, *Journal of Physical Chemistry B*, 110, 4318, 2006.

M. Basu et al., Nano-biosensor development for bacterial detection during human kidney infection: use of glycoconjugatespecific antibody-bound gold NanoWire arrays (GNWA), *Glycoconjugate Journal*, 21, 487, 2004.

S. Mann et al., Carbon nanotube-templated self-assembly and thermal processing of gold nanowires, *Advanced Materials*, 12, 1430, 2000.

S. Connolly et al., Effects of ligand-receptor geometry and stoichiometry on protein-induced aggregation of biotin-modified colloidal gold, *Journal of Physical Chemistry B*, 105, 2222, 2001.

B. S. McEwen, Stress, adaptation, and disease. Allostasis and allostatic load, *Ann. N. Y. Acad. Sci.* 840 (1998) 33-44. http://www.ncbi.nlm.nih.gov/pubmed/9629234 (accessed Oct. 8, 2015).

R. Wilkinson, M. Marmot, Social Determinants of Health, OUP Oxford, 1999. https://books.google.com/books?hl=en&lr=&id=AmwiS8HZeRIC&pgis=1 (accessed Feb. 4, 2016).

J. F. P. Peres, B. Foerster, L. G. Santana, M. D. Fereira, A. G. Nasello, M. Savoia, et al., Police officers under attack: resilience implications of an fMRI study, J. Psychiatr. Res. 45 (2011) 727-34. doi:10.1016/j.jpsychires.2010.11.004.

S. A. Snipes, B. Thompson, K. O'Connor, B. Shell-Duncan, D. King, A. P. Herrera, et al., "Pesticides protect the fruit, but not the people": using community-based ethnography to understand farmworker pesticide-exposure risks, Am. J. Public Health. 99 Suppl 3 (2009) S616-21. doi:10.2105/AJPH.2008.148973.

A. Cecchi, M. G. Rovedatti, G. Sabino, G. G. Magnarelli, Environmental exposure to organophosphate pesticides: assessment of endocrine disruption and hepatotoxicity in pregnant women, Ecotoxicol. Environ. Saf. 80 (2012) 280-7. doi:10.1016/j.ecoenv.2012.03.008.

E. M. Clingerman, A. Brown, Stress in migrant farmworkers during premigration, Biol. Res. Nurs. 14 (2012) 27-37. doi:10.1177/1099800410396703.

R. Fraser, M. C. Ingram, N. H. Anderson, C. Morrison, E. Davies, J. M. C. Connell, Cortisol Effects on Body Mass, Blood Pressure, and Cholesterol in the General Population, Hypertension. 33 (1999) 1364-1368.

D. S. Charney, Psychobiological Mechanism of Resilience and Vulnerability: Implications for Successful Adaptation to Extreme Stress, Am. J. Psychiatry. 161 (2004) 195-216. doi:10.1176/appi.ajp.161.2.195.

M. van Eck, H. Berkhof, N. Nicolson, J. Sulon, The effects of perceived stress, traits, mood states, and stressful daily events on salivary cortisol, Psychosom. Med. 58 447-58. http://www.ncbi.nlm.nih.gov/pubmed/8902896 (accessed Feb. 4, 2016).

S. Choi, S. Kim, J.-S. Yang, J.-H. Lee, C. Joo, H.-I. Jung, Real-time measurement of human salivary cortisol for the assessment of psychological stress using a smartphone, Sens. Bio-Sensing Res. 2 (2014) 8-11. doi:10.1016/j.sbsr.2014.08.001.

M. Yamaguchi, H. Katagata, Y. Tezuka, D. Niwa, V. Shetty, Automated-immunosensor with centrifugal fluid valves for salivary cortisol measurement, Sens. Bio-Sensing Res. 1 (2014) 15-20. doi:http://dx.doi.org/10.1016/j.sbsr.2014.07.001.

M. Zangheri, L. Cevenini, L. Anfossi, C. Baggiani, P. Simoni, F. Di Nardo, et al., A simple and compact smartphone accessory for quantitative chemiluminescence-based lateral flow immunoassay for salivary cortisol detection, *Biosens. Bioelectron.* 64 (2015) 63-8. doi: 10.1016/j.bios.2014.08.048.

K. Haupt, K. Mosbach, Molecularly imprinted polymers and their use in biomimetic sensors, Chem. Rev. 100 (2000) 2495-504. http://www.ncbi.nlm.nih.gov/pubmed/11749293 (accessed Jun. 10, 2015).

M. J. Whitcombe, I. Chianella, L. Larcombe, S. A. Piletsky, J. Noble, R. Porter, et al., The rational development of molecularly imprinted polymer-based sensors for protein detection, Chem. Soc. Rev. 40 (2011) 1547-71. doi: 10.1039/c0cs00049c.

K. K. Reddy, K. V. Gobi, Artificial molecular recognition material based biosensor for creatinine by electrochemical impedance analysis, Sensors Actuators B Chem. 183 (2013) 356-363. doi:10.1016/j.snb.2013.04.015.

G. Vlatakis, L. I. Andersson, R. Miller, K. Mosbach, Drug assay using antibody mimics made by molecular imprinting, Nature. 361 (1993) 645-7. doi:10.1038/361645a0.

A. Poma, A. Guerreiro, M. J. Whitcombe, E. V Piletska, A. P. F. Turner, S. A. Piletsky, Solid-Phase Synthesis of Molecularly Imprinted Polymer Nanoparticles with a Reusable Template—"Plastic Antibodies", Adv. Funct. Mater. 23 (2013) 2821-2827. doi: 10.1002/adfm.201202397.

C. Malitesta, F. Palmisano, L. Torsi, P. G. Zambonin, Glucose fast-response amperometric sensor based on glucose oxidase immobilized in an electropolymerized poly(o-phenylenediamine) film, Anal. Chem. 62 (1990) 2735-2740. doi:10.1021/ac00223a016.

M. C. Blanco-López, S. Gutiérrez-Fernández, M. J. Lobo-Castañón, A. J. Miranda-Ordieres, P. Tuñón-Blanco, Electrochemical sensing with electrodes modified with molecularly imprinted polymer films, Anal. Bioanal. Chem. 378 (2004) 1922-8. doi:10.1007/s00216-003-2330-2.

N. Karimian, A. P. F. Turner, A. Tiwari, Electrochemical evaluation of troponin T imprinted polymer receptor, Biosens. Bioelectron. 59 (2014) 160-165. doi:10.1016/j.bios.2014.03.013.

B. L. Li, J. H. Luo, H. Q. Luo, N. B. Li, A novel strategy for selective determination of d-penicillamine based on molecularly imprinted polypyrrole electrode via the electrochemical oxidation with ferrocyanide, Sensors Actuators, B Chem. 186 (2013) 96-102. doi:10.1016/j.snb.2013.05.091.

L. Özcan, Y. Şahin, Determination of paracetamol based on electropolymerized-molecularly imprinted polypyrrole modified pencil graphite electrode, Sensors Actuators, B Chem. 127 (2007) 362-369. doi:10.1016/j.snb.2007.04.034.

N. Murase, S. Taniguchi, E. Takano, Y. Kitayama, T. Takeuchi, A molecularly imprinted nanocavity-based fluorescence polarization assay platform for cortisol sensing, J. Mater. Chem. B. (2016). doi: 10.1039/C5TB02069G.

O. Ramström, L. Ye, K. Mosbach, Artificial antibodies to corticosteroids prepared by molecular imprinting, Chem. Biol. 3 (1996) 471-477. doi: 10.1016/S1074-5521(96)90095-2.

C. Baggiani, P. Baravalle, C. Giovannoli, L. Anfossi, G. Giraudi, Molecularly imprinted polymers for corticosteroids: Analysis of binding selectivity, Biosens. Bioelectron. 26 (2010) 590-595. doi:10.1016/j.bios.2010.07.023.

R. A. Lorenzo, A. M. Carro, C. Alvarez-Lorenzo, A. Concheiro, To remove or not to remove? The challenge of extracting the template to make the cavities available in Molecularly Imprinted Polymers (MIPs), Int. J. Mol. Sci. 12 (2011) 4327-47. doi:10.3390/ijms12074327.

M. Pandiaraj, T. Madasamy, P. N. Gollavilli, M. Balamurugan, S. Kotamraju, V. K. Rao, et al., Nanomaterial-based electrochemical biosensors for cytochrome<i> c</i> using cytochrome<i> c</i> reductase, Bioelectrochemistry. 91 (2013) 1-7.

Y. Li, R. Qian, Electrochemical overoxidation of conducting polypyrrole nitrate film in aqueous solutions, Electrochim. Acta. 45 (2000) 1727-1731. doi: 10.1016/S0013-4686(99)00392-8.

S. Tunn, G. Pappert, P. Willnow, M. Krieg, Multicentre evaluation of an enzyme-immunoassay for cortisol determination, Clin. Chem. Clin. Biochem. 28 (1990) 929-35. http://www.ncbi.nlm.nih.gov/pubmed/2081964 (accessed Dec. 25, 2015).

I. A. Ionita, D. M. Fast, F. Akhlaghi, Development of a sensitive and selective method for the quantitative analysis of cortisol, cortisone, prednisolone and prednisone in human plasma, J. Chromatogr. B. Analyt. Technol. Biomed. Life Sci. 877 (2009) 765-72. doi: 10.1016/j.jchromb.2009.02.019.

M. D. Krasowski, D. Drees, C. S. Morris, J. Maakestad, J. L. Blau, S. Ekins, Cross-reactivity of steroid hormone immunoassays: clinical significance and two-dimensional molecular similarity prediction, BMC Clin. Pathol. 14 (2014) 33. doi:10.1186/1472-6890-14-33.

S. Piletsky, E. Piletska, K. Karim, G. Foster, C. Legge, A. Turner, Custom synthesis of molecular imprinted polymers for biotechnological application, Anal. Chim. Acta. 504 (2004) 123-130. doi: 10.1016/S0003-2670(03)00814-6.

S. K. Pasha, a. Kaushik, a. Vasudev, S. a. Snipes, S. Bhansali, Electrochemical Immunosensing of Saliva Cortisol, J. Electrochem. Soc. 161 (2013) B3077-B3082. doi:10.1149/2.017402jes.

Bard, Allen J. LRF (2000) Electrochemical Methods: Fundamentals and Applications. Wiley; 2 edition.

What is claimed is:

1. An electrochemical sensing substrate for detecting a target analyte, said sensing substrate comprising a plurality of metallic nanoscopic structures deposited onto a surface of the sensing substrate, the surface further comprising a layer of conductive polymer matrix film deposited on top of the metallic nanoscopic structures, the polymer matrix film being embedded with a plurality of molecular recognition sites structurally and functionally complementary to the target analyte, the detection of the target analyte using the sensing substrate requiring no external redox labels or mediators, and the target analyte being a steroid hormone.

2. The device, according to claim 1, wherein the target analyte is cortisol.

3. A method of fabricating an electrochemical sensing substrate for detecting a target analyte, comprising:
providing a conductive electrode;
depositing a layer of conductive polymer matrix film onto a surface of the electrode in the presence of the target analyte by electro-polymerization; and
eluting the target analyte from the layer of polymer matrix film, wherein the detection of the target analyte using the sensing substrate requires no external redox labels or mediators, the target analyte being a steroid hormone selected from cortisol, progesterone, testosterone, estradiol, and aldosterone; an amino acid selected from tyrosine, cysteine, glutamine, and phenylalanine; a small molecule with a molecular weight of less than 875 Da selected from lactate and glucose; a protein; cell; a toxin; or a virus.

4. The method according to claim 3, wherein the target analyte is cortisol.

5. The method according to claim 3, wherein the target analyte is cortisol.

6. An electrochemical sensing substrate for detecting a target analyte, comprising at a surface of the sensing substrate a layer of conductive polymer matrix film, characterized in that the polymer matrix film is embedded with a plurality of molecular recognition sites structurally and functionally complementary to the target analyte, wherein the target analyte is cortisol.

7. A method of fabricating an electrochemical sensing substrate for detecting a target analyte, comprising:
providing a conductive electrode;
depositing a layer of conductive polymer matrix film onto the surface of the electrode in the presence of the target analyte by electro-polymerization; and
eluting the target analyte from the layer of polymer matrix film, wherein the target analyte is cortisol.

8. A method of detecting a target analyte, comprising:
providing a biological sample, characterized in that the sample is a human physiological fluid selected from blood, plasma, serum, saliva, urine, mucous, and tears;
contacting the sample with an electrochemical sensing device, the device comprising a working electrode, a counter electrode, and a reference electrode, characterized in that the working electrode is a sensing substrate comprising at a surface thereof a layer of conductive polymer matrix film and optionally a plurality of nanoscopic metallic structures, and further characterized in that the conductive polymer matrix film is embedded with a plurality of molecular recognition sites structurally and functionally complementary to the target analyte;
applying voltage to the sensing device;
monitoring the current response of the device as the target analyte binds with the sensing substrate; and
eluting any bound target analyte by electrochemically overoxidizing the sensing substrate, wherein the target analyte is cortisol.

* * * * *